(12) United States Patent
Kano et al.

(10) Patent No.: US 7,928,034 B2
(45) Date of Patent: Apr. 19, 2011

(54) PROCESS FOR PRODUCING OLEFIN OXIDE

(75) Inventors: Hirotsugu Kano, Ibaraki (JP); Michio Yamamoto, Otsu (JP); Makoto Yako, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 571 days.

(21) Appl. No.: 11/816,957

(22) PCT Filed: Feb. 16, 2006

(86) PCT No.: PCT/JP2006/303203
§ 371 (c)(1),
(2), (4) Date: Aug. 23, 2007

(87) PCT Pub. No.: WO2006/090754
PCT Pub. Date: Aug. 31, 2006

(65) Prior Publication Data
US 2009/0216034 A1 Aug. 27, 2009

(30) Foreign Application Priority Data
Feb. 25, 2005 (JP) .................... 2005-050663

(51) Int. Cl.
*B01J 23/50* (2006.01)
*C07D 301/03* (2006.01)

(52) U.S. Cl. ...................... 502/347; 549/537

(58) Field of Classification Search .............. 549/537; 502/347
See application file for complete search history.

(56) References Cited

U.S. PATENT DOCUMENTS

| | | | |
|---|---|---|---|
| 4,845,253 A | 7/1989 | Bowman | |
| 4,908,343 A | 3/1990 | Bhasin | |
| 5,618,954 A | 4/1997 | Boeck et al. | |
| 5,625,084 A | 4/1997 | Pitchai et al. | |
| 5,703,254 A | 12/1997 | Gaffney et al. | |
| 5,763,630 A | 6/1998 | Kahn et al. | |
| 5,770,746 A | 6/1998 | Cooker et al. | |
| 5,780,657 A | 7/1998 | Cooker et al. | |
| 5,856,534 A | 1/1999 | Cooker et al. | |
| 5,861,519 A | 1/1999 | Kahn et al. | |
| 5,864,047 A | 1/1999 | Gaffney | |
| 6,372,925 B1 | 4/2002 | Evans et al. | |
| 6,392,066 B1 | 5/2002 | Mul et al. | |
| 2005/0113587 A1 | 5/2005 | Yako et al. | |

FOREIGN PATENT DOCUMENTS

| | | |
|---|---|---|
| CN | 1535962 A | 10/2004 |
| DE | 1124030 B | 2/1962 |
| EP | 1393801 A1 | 3/2004 |
| EP | 1462446 A2 | 9/2004 |
| GB | 1368922 | 10/1974 |
| JP | 01-231942 A | 9/1989 |
| JP | 02-241544 A | 9/1990 |
| JP | 07-000820 A | 1/1995 |
| JP | 2002-510306 A | 4/2002 |
| JP | 2004-307485 A | 11/2004 |
| WO | WO 97/28142 A1 | 8/1997 |
| WO | WO 97/34693 A1 | 9/1997 |
| WO | WO 98/30552 A1 | 7/1998 |
| WO | WO 98/45280 A1 | 10/1998 |
| WO | WO 98/52931 A1 | 11/1998 |
| WO | WO 98/58920 A1 | 12/1998 |
| WO | WO 98/58921 A1 | 12/1998 |
| WO | WO 99/32471 A1 | 7/1999 |
| WO | WO 01/96324 A2 | 12/2001 |

OTHER PUBLICATIONS

Zemichael et al., "Propene epoxidation over K-promoted Ag/CaCO3 catalysts: the effect of metal particle size", Catalysis Letters, 2002, 80(3-4), Plenum Publishing Company.
Supplementary European Search Report issued by European Patent Office dated Jun. 18, 2009 for European Patent Application No. 06 71 4343.
Office Action mailed Nov. 20, 2009 received in China Application No. 200680012785.8, with translation (9 pgs.).

*Primary Examiner* — Janet L. Andres
*Assistant Examiner* — Raymond Covington
(74) *Attorney, Agent, or Firm* — Foley & Lardner LLP

(57) ABSTRACT

There is disclosed a process for producing an olefin oxide characterized by contacting an olefin and oxygen, in the presence of water and a halogen compound, with a silver catalyst, wherein the silver catalyst is a silver catalyst that is obtainable by contacting metal silver, a silver compound or a mixture of both with an alkaline earth metal carbonate and that has an alkali metal content of 1,500 ppm or less based on the total weight of the silver catalyst.

10 Claims, No Drawings

PROCESS FOR PRODUCING OLEFIN OXIDE

TECHNICAL FIELD

The present invention relates to a process for producing an olefin oxide.

BACKGROUND ART

Olefin oxides represented by propylene oxide are industrially important as intermediate materials of industrial chemicals, synthetic resins, rubbers or the like. As the process for producing such an olefin, non-patent Document 1 (p. 95, FIG. 1) discloses a process in which olefin is reacted with oxygen in the presence of a catalyst containing silver supported on calcium carbonate and potassium as an promoter and that about 2% of a potassium promoter contained in the catalyst is important to improve selectivity of propylene oxide and decrease of potassium content in the catalyst led to remarkable decrease of the selectivity. Patent Document 1 discloses an oxidation of propylene using a catalyst containing a potassium promoter. In addition, a catalyst containing a silver salt supported on a silicate in which sodium silicate is used as a raw material, and a silver catalyst containing silver supported on alumina are known (Patent Documents 2 and 3). Furthermore, a process for producing an olefin oxide, in which water is added to a reaction gas is also disclosed (Patent Document 4). However, selectivity of olefin oxide in these processes is not always satisfactory, and a further improvement has been required from an industrial point of view.

Patent Document 1: JP-T 2002-510306
Patent Document 2: JP-A 1-231942
Patent Document 3: GB 1,368,922
Patent Document 4: JP-A 2004-307485
Non-patent Document 1: Catalysis Letters, June 2002, Vol. 80, 3-4, pp. 93-98

DISCLOSURE OF THE INVENTION

According to the present invention an olefin oxide can be produced with good selectivity, and the process is industrially advantageous. That is, the present invention provides a process for producing an olefin oxide comprising contacting an olefin and oxygen, in the presence of water and a halogen compound, with a silver catalyst (hereinafter referred to as a silver catalyst of the present invention), wherein the silver catalyst is a silver catalyst that is obtainable by contacting silver metal, a silver compound or a mixture of both with an alkaline earth metal carbonate and that has an alkali metal content of 1,500 ppm or less based on the total weight of the silver catalyst.

BEST MODE FOR CARRYING OUT OF THE INVENTION

The silver catalyst of the present invention will be explained below.

The silver catalyst of the present invention usually contains silver in an amount of 0.1% by weight or more, preferably 0.5% by weight or more, based on the total weight of the silver catalyst.

The silver catalyst of the present invention is prepared as a silver-containing composition by contacting silver metal, a silver compound or a mixture of both with an alkaline earth metal carbonate. Alternatively, the silver catalyst may be prepared by further contacting at least one selected from the group consisting of an acid and a nitrogen-containing compound, with the resulting silver-containing composition. The silver catalyst of the present invention also encompasses silver-containing calcined products obtainable by calcining such silver-containing compositions or by calcining a composition obtainable by contacting at least one selected from the group consisting of an acid and a nitrogen-containing compound, with the silver-containing composition.

In order to sufficiently exert the effect of the present invention, the total content of alkali metal(s) such as lithium, sodium, potassium, rubidium, cesium or the like contained in the silver catalyst of the present invention is 1,500 ppm or less, and preferably 900 ppm or less based on the total weight of the silver catalyst.

Examples of the silver compound include, for example, silver oxide, silver carbonate, silver nitrate, silver sulfate, silver cyanide, silver chloride, silver bromide, silver iodide, silver acetate, silver benzoate, silver acetylacetonate, silver lactate, and the like.

The silver metal that can be obtainable by contacting a silver compound with a reducing agent in a gas phase or a liquid phase may also be used.

In case of reducing the silver compound, exemplified reducing agents include a reducing gas such as hydrogen or the like; alcohols such as methanol, ethanol, propanol, butanol, ethylene glycol, propylene glycol, glycerol, amino ethanol, dimethylamino ethanol or the like; saccharides such as glucose, fructose, galactose or the like; aldehydes such as formaldehyde, acetaldehyde, propylaldehyde, butyraldehyde, phenylaldehyde or the like; hydrazines such as hydrazine, methylhydrazine, ethylhydrazine, propylhydrazine, butylhydrazine, phenylhydrazine or the like; metal hydrides such as lithium hydride, sodium hydride, potassium hydride, calcium hydride, magnesium hydride or the like; boron compounds such as boron hydride, sodium borohydride, potassium borohydride, dimethylamine borane or the like; and phosphates such as sodium hydrogen phosphite, potassium hydrogen phosphite, and the like. The reduction of the silver compound is preferably conducted in a gas phase condition, and steam can be added in the gas phase condition. An amount of the reducing agent that may be used is usually from about 0.1 to 20 moles per mole of the silver compound to be reduced. A reduction temperature is usually from −30° C. to 300° C., and preferably from 0° C. to 200° C.

Examples of the carbonate of an alkaline earth metal include, for example, magnesium carbonate, calcium carbonate, strontium carbonate, barium carbonate and the like, and preferred are calcium carbonate, strontium carbonate or barium carbonate. The alkaline earth metal carbonate having a specific surface area, as measured by nitrogen absorption using a BET method, of from 10 m$^2$/g to 70 m$^2$/g is preferably used. Further, in order to prevent contamination of more than the required amount of alkali metal into the silver catalyst and make the amount of alkali metal to the prescribed amount as above, the alkaline earth metal carbonate containing 1,500 ppm or less of an alkali metal such as lithium, sodium, potassium, rubidium, cesium or the like, is preferably used. The alkaline earth metal carbonate having reduced amount of alkali metal contents by washing with water, an organic acid, an inorganic acid, or a mixture thereof can also be used.

A rare earth metal carbonate such as scandium carbonate, yttrium carbonate, cerium carbonate, or ytterbium carbonate can be added to the alkaline earth metal carbonate. The amount of the alkaline earth metal carbonate when used alone, and the total amount of the alkaline earth metal carbonate and the rare earth metal carbonate when the rare earth metal carbonate is added to the alkaline earth metal carbonate, are usually from 0.1 to 120 parts by weight per 1 part by weight of silver in silver metal, a silver compound, or the mixture of both.

The acid may be an inorganic acid or an organic acid, and preferably used is the organic acid. Examples of the inorganic acid include, for example, hydrochloric acid, nitric acid, nitrous acid, sulfuric acid, perchloric acid and the like. Examples of the organic acid include, for example, aliphatic carboxylic acids such as acetic acid, oxalic acid, propionic acid, butyric acid, citric acid, maleic acid, fumaric acid, tartaric acid or the like, and aromatic carboxylic acids such as benzoic acid, dicarboxybenzene, tricarboxybenzene, dicarboxynaphthalene, dicarboxyanthracene or the like. Preferred is an aliphatic carboxylic acid, and among them oxalic acid and citric acid are preferred The acid that may be used to prepare the silver catalyst of the present invention may be either an inorganic acid or an organic acid, but is preferably an organic acid. Examples of the inorganic acid include, for example, hydrochloric acid, nitric acid, nitrous acid, sulfuric acid, and perchloric acid. Examples of the organic acid include, for example, aliphatic carboxylic acids such as acetic acid, oxalic acid, propionic acid, butyric acid, citric acid, maleic acid, fumaric acid, and tartaric acid, and aromatic carboxylic acids such as benzoic acid, dicarboxybenzene, tricarboxybenzene, dicarboxynaphthalene, and dicarboxyanthracene. Among these organic acids, an aliphatic carboxylic acid is preferred, and oxalic acid and citric acid are preferred.

The amount of the acid that may be used is usually from 0.1 to 10 moles per mole of silver in silver metal, a silver compound, or a mixture of both.

Examples of the nitrogen-containing compound that may be used to prepare the silver catalyst of the present invention include, for example, nitrogen-containing organic compounds such as an amine compound, an imine compound, an amide compound, a hydrazine compound, a nitrile compound, a nitro compound, a nitroso compound or the like, nitrogen-containing inorganic compounds such as ammonia, hydroxylamine, hydrazine, hydroxylamine hydrochloride or the like, and a quaternary ammonium salt. Among these compounds, the amine compound is preferred. Among the nitrogen-containing compounds, adduct salts with acid such as amine hydrochloride or amine acetate may exist and such acid adduct salts may also be used. The amount of the nitrogen-containing compound is from 0.1 moles to 20 moles per mole of silver in silver metal, a silver compound or a mixture of both.

Examples of the amine compound include, for example, aliphatic or aromatic amines having 1 to 20 carbon atoms, such as methylamine, ethylamine, propylamine, butylamine, amylamine, hexylamine, heptylamine, octylamine, decylamine, dodecylamine, stearylamine, dimethylamine, diethylamine, dipropylamine, dibutylamine, trimethylamine, triethylamine, ethanolamine, dimethylethanolamine, diethanolamine, triethanolamine, ethylenediamine, tetramethylenediamine, pentamethylenediamine, diethylenetriamine, aniline, benzylamine, and phenylenediamine. The examples also include, an amino acid such as glycine or the like.

Examples of the imine compound include, for example, ethyleneimine, pyrrolidine, piperidine, piperazine and the like.

Examples of the amide compound include, for example, acetamide, benzamide and the like.

Examples of the hydrazine compound include, for example, hydrazine, methylhydrazine, phenylhydrazine and the like.

Examples of the nitrile compound include, for example, benzonitrile, butyronitrile and the like.

Examples of the nitro compound include, for example, nitrobenzene, nitropyridine and the like.

Examples of the nitroso compound include, for example, nitrosodimethylaniline, nitrosonaphthol and the like.

Examples of the quaternary ammonium salt include, for example, quaternary ammonium hydroxides such as tetramethylammonium hydroxide, tetraethylammonium hydroxide, tetrapropylammonium hydroxide or the like, and quaternary ammonium halides such as tetramethylammonium chloride, tetramethylammonium bromide, tetraethylammonium chloride, tetraethylammonium bromide or the like.

A composition that can be used as a silver catalyst can be obtained by contacting, (mixing) silver metal, a silver compound or a mixture of both, and an alkaline earth metal carbonate, and optionally at least one selected from the group consisting of an acid and a nitrogen-containing compound, in a solvent such as water, methanol, ethanol, propanol, tetrahydrofuran, toluene, hexane, or a mixture of the solvents, for example, at 0 to 200° C., and optionally filtering the mixture, followed by concentration. In addition, silver metal can be prepared by contacting a silver compound and a reducing agent in a gas phase or in a solvent such as water, methanol or the like at 0° C. to 300° C.

Alternatively, the silver catalyst of the present invention can be prepared as a silver-containing calcined product by calcining the composition above. The calcination is carried out, for example, by subjecting the silver-containing composition obtained by the above-described process to a heating treatment at 20° C. to 700° C. in a flow of hydrogen, nitrogen, air, carbon monoxide, carbon dioxide, methane, ethane, propane, butane, ethylene, propylene, butene, butadiene or the like alone or in a combined flow thereof. In the flow, stream is preferably mixed. The amount of steam in the flow can be determined for every treatment, but is preferably from 5% to 70% (as a volume of steam in the whole flow volume). When steam is mixed in the flow, the calcination temperature is preferably from 70 to 250° C. The silver-containing composition may be molded and then calcined, or the calcined composition may be molded thereafter.

Next, a process for producing an olefin oxide comprising contacting a reaction gas containing olefin and oxygen with the silver catalyst in the presence of water and a halogen compound will be described (hereinafter referred to as the present reaction).

The present reaction can be carried out in a batch-wise or continuously, but is preferably carried out continuously from an industrial viewpoint.

The silver catalyst of the present invention is used in the effective amount or more as a catalyst, and is usually 0.00005 mol or more, in terms of silver metal, per mole of the olefin. The upper limit is not especially limited, but can be adjusted considering economical efficiency.

The amount of water is usually from 0.1 mole to 20 moles, preferably from 0.2 to 10 moles, and more preferably from 0.3 moles to 8 moles, per mole of the olefin. The water may be steam.

The halogen compound is preferably a saturated or unsaturated organohalogen compound capable of existing as a gas under the conditions of temperature and pressure in the reaction system. More specifically, examples of the saturated or unsaturated halogen compound include, for example, an organic fluorine compound, an organic chlorine compound, an organic bromine compound and an organic iodine compound. More preferably, an organic chlorine compound is used, and the compound includes, for example, ethyl chloride, 1,2-ethylene dichloride, methyl chloride, and vinyl chloride.

The optimum amount of the halogen compound to be supplied varies depending on factors such as a concentration of olefin, a concentration of oxygen, an amount of a silver catalyst, and an amount of water to be used, but is usually from 1 ppm to 1,000 ppm, and preferably from 1 ppm to 500 ppm, in the entire reaction gas excluding water.

Examples of the olefin include, for example, olefin having 2 to 6 carbon atoms such as ethylene, propylene, 1-butene, 2-butene, isobutene, 1-pentene or the like. Propylene is preferred.

The olefin can be used as it is, or used as a gas mixture of the olefin and an inert gas such as nitrogen, helium, argon, carbon dioxide or the like. When the amount of the inert gas is too much, the concentration of olefin and oxygen in the reaction becomes too low, and thus the reaction rate decreases. Thus, the practical amount of the inert gas is usually 50 moles or less per mole of the olefin.

Oxygen can be used alone or as a gas mixture with an inert gas such as air or the like. The amount of oxygen varies depending on a reaction types a kind of a catalyst, a reaction temperature and the like, but is usually from 0.01 mole to 100 moles, and preferably from 0.03 mole to 30 moles, per mole of the olefin.

The reaction temperature is usually from 100° C. to 400° C., and preferably from 120° C. to 300° C.

The present reaction is carried out under the reaction pressure from reduced pressure to pressurized pressure. When water and a halogen compound are co-existed under such the reaction pressure condition, productivity and selectivity of olefin oxide can be increased. The reduced pressure herein means that the reaction pressure is reduced to a pressure below the atmospheric pressure, and the pressurized pressure means that the reaction pressure is pressurized to a pressure above the atmospheric pressure. Such a pressure condition of from the reduced pressure to the pressurized pressure is usually within a range from 0.01 MPa to 3 MPa, and preferably from 0.02 MPa to 2 MPa, in terms of an absolute pressure.

The present reaction is carried out by mixing and/or contacting the silver catalyst, water, olefin, oxygen and a halogen compound under the reduced pressure to the pressurized pressure.

After completion of the reaction, a reaction liquid or a reaction gas is collected, and the desired olefin oxide can be obtained by conventional separation methods such as distillation or the like.

The olefin oxide obtained by the above-described process includes, for example, ethylene oxide, propylene oxide, butene oxide, or pentene oxide corresponding to the employed olefin such as ethylene, propylene, butene or pentene.

EXAMPLES

The present invention will be described in detail by way of Examples, but the present invention is not limited to these Examples.

Reference Example 1

100 g of an aqueous silver nitrate solution containing 10 g of silver nitrate was added dropwise to 245.0 g of a slurry solution containing 23.5 g of strontium carbonate having a surface area of 6.7 m$^2$/g and an alkaline metal content of 20 ppm or less (manufactured by SAKAI CHEMICAL INDUSTRY CO., LTD., under the trade name of SW-K) as alkaline earth metal carbonate at 20° C. to 25° C., followed by stirring for 3 hours. The solid was collected by filtration, washed with 200 mL of ion exchanged water four times to obtain 193 g of a silver carbonate/strontium carbonate mixture. Then, a sliver catalyst was prepared by filling the resulting silver carbonate/strontium carbonate mixture in a calcinations glass tube, followed by subjecting to calcination at 350° C. for 3 hours under an air flow of 100 mL/min.

Example 1

1 mL of the silver catalyst obtained in Reference Example 1 was filled in a stainless steel reaction tube with ½ inches in diameter. Propylene (feed rate of 450 mL/Hr), an air (feeding rate of 900 mL/Hr), a nitrogen gas (feed rate of 990 mL/Hr), water (feed rate of 1.2 mL/Hr) and ethyl chloride (140 ppm) were fed to the reaction tube and then reacted at a reaction temperature of 200° C. under the pressurized pressure (corresponding to 0.4 MPa in terms of an absolute pressure). A propylene conversion was 0.7% and a propylene oxide selectivity was 40%.

Comparative Example 1

A catalyst was prepared in a similar manner as in Reference Example 1, except that calcium carbonate (manufactured by MARUO CALCIUM CO., LTD., under the trade name of CUBE-50KA) was used as the alkaline earth metal carbonate containing 2,800 ppm of alkaline metal. The results of elemental analysis revealed that the resulting silver catalyst contains 1,900 ppm of alkali metal. The resulting catalyst was used in the reaction in a similar manner as in Example 1. As a result, a propylene conversion was 0.6%, and propylene oxide selectivity was 4%.

Reference Example 2

200 g of an aqueous silver nitrate solution containing 52 g of silver nitrate was added dropwise to 1,200.0 g of a slurry solution containing 115.3 g of calcium carbonate having a surface area of 0.4 m$^2$/g and an alkali metal content of 20 ppm or less (reagent distributed by Nacalai Tesque, Inc.) as alkaline earth metal carbonate at 20° C. to 25° C., followed by stirring for 3 hours. The solid was collected by filtration, washed with 200 mL of ion exchanged water four times to obtain 193 g of a silver carbonate/calcium carbonate mixture. Then, 48.3 g of the resulting silver carbonate/calcium carbonate mixture and 25 g of ion exchanged water were put into a flask, and adding 5.2 g of ethylenediamine, 5.4 g of oxalic acid and 1.8 g of monoethanolamine, followed by stirring for one hour, and further dried at 70° C. under reduced pressure. Then, a silver catalyst was prepared by filling the obtained powder into a calcination glass tube, and subjecting the powder to calcination at 350° C. for 3 hours under air flow of 100 mL/min.

Example 2

1 mL of the silver catalyst obtained in Reference Example 2 was filled in a stainless steel reaction tube with ½ inches in diameter. Propylene (feed rate of 450 mL/Hr), an air (feed rate of 900 mL/Hr), a nitrogen gas (feed rate of 990 mL/Hr) water and ethyl chloride (concentration of ethyl chloride in the fed raw material except water as shown in Table 1) were fed to the reaction tube and then reacted at a temperature of 200° C.

under the pressurized pressure (corresponding to 0.4 MPa in terms of an absolute pressure). The results are shown in Table 1.

TABLE 1

|  | Example 2 | Comparative Example 2 | Comparative Example 3 | Comparative Example 4 |
|---|---|---|---|---|
| Water feed (mL/Hr) | 1.2 | 1.2 | 0 | 0 |
| Ethyl chloride feed (ppm) | 140 | 0 | 140 | 0 |
| Propylene conversion (%) | 0.9 | 8.5 | 1.2 | 0.4 |
| Ppropylene oxide selectivity (%) | 37 | 6 | 10 | 8 |

Comparative Example 2

A similar operation as in Example 2 was carried out, except that ethyl chloride was not used. The results are shown in Table 1.

Comparative Example 3

A similar operation as in Example 2 was carried out, except that water was not fed. The results are shown in Table 1.

Comparative Example 4

A similar operation as in Example 2 was carried out, except that water and ethyl chloride were not fed. The results are shown in Table 1.

Examples 3 to 6

A similar operation as in Example 2 was carried out, except that water was fed at the feed rate shown in Table 2. The results are shown in Table 2.

TABLE 2

|  | Example 3 | Example 4 | Example 5 | Example 6 |
|---|---|---|---|---|
| Water feed (mL/Hr) | 0.12 | 0.36 | 0.6 | 2.4 |
| Ethyl chloride feed (ppm) | 140 | 140 | 140 | 140 |
| Propylene conversion (%) | 0.2 | 0.2 | 0.3 | 0.5 |
| propylene oxide selectivity (%) | 24 | 29 | 34 | 23 |

Example 7

A similar operation as in Example 2 was carried out, except that the concentration of ethyl chloride was 280 ppm in Example 2. A propylene conversion was 0.4% and propylene oxide selectivity was 38%.

Example 8

2 mL of the silver catalyst obtained in Reference Example 2 was filled in a glass reaction tube having an inner diameter of 10 ma. Propylene (feed rate of 360 mL/Hr), an air (feed rate of 360 mL/Hr), and water and ethyl chloride (feed rates and concentration are shown in Table 3, respectively) were fed to the reaction tube and then reacted at a temperature of 200° C. under atmospheric pressure (corresponding to 0.1 MPa in terms of an absolute pressure). The results are shown in Table 3.

TABLE 3

|  | Example 8 | Comparative Example 5 | Comparative Example 6 | Comparative Example 7 |
|---|---|---|---|---|
| Water feed (mL/Hr) | 1.0 | 1.0 | 0 | 0 |
| Ethyl chloride feed (ppm) | 130 | 0 | 70 | 0 |
| Propylene conversion (%) | 0.5 | 3.8 | 0.1 | 0.4 |
| Propylene oxide selectivity (%) | 33 | 13 | 16 | 11 |

Comparative Example 5

A similar operation as in Example 8 was carried out, except that ethyl chloride was not fed. The results are shown in Table 3.

Comparative Example 6

A similar operation as in Example 8 was carried out, except that water was not fed and the concentration of ethyl chloride in the fed raw material was 70 ppm. The results are shown in Table 3.

Comparative Example 7

A similar operation as in Example 8 was carried out, except that water and ethyl chloride were not fed. The results are shown in Table 3.

Example 9

A catalyst was prepared in a similar manner as in Reference Example 1, except that calcium carbonate having a surface area of 46.5 m$^2$/g and an alkali metal content of 20 ppm or less (manufactured by SAKAI CHEMICAL INDUSTRY CO., LTD. under the trade name of CWS-50) was used as an alkaline earth metal carbonate. The reaction was carried out in a similar manner as in Example 1. The results are shown in Table 4.

Example 10

A catalyst was prepared in a similar manner as in Reference Example 1, except that calcium carbonate having a surface area of 20.5 m$^2$/g and an alkali metal content of 20 ppm or less (manufactured by SAKAI CHEMICAL INDUSTRY CO., LTD under the trade name of CWS-20) was used as an alkaline earth metal carbonate. The reaction was carried out in a similar manner as in Example 1. The results were shown in Table 4.

TABLE 4

|  | Example 9 | Example 10 |
|---|---|---|
| Propylene conversion (%) | 2.2 | 1.3 |
| propylene oxide selectivity (%) | 36 | 36 |

Example 11

A catalyst was prepared in a similar manner as in Reference Example 1, except that strontium carbonate having a surface area of 19.0 m²/g and an alkali metal content of 20 ppm or less (manufactured by SAKAI CHEMICAL INDUSTRY CO., LTD under the trade name of SW-K20) was used as an alkaline earth metal carbonate. The reaction was carried out in a similar manner as in Example 1. The results are shown in Table 5.

Example 12

A catalyst was prepared in a similar manner as in Reference Example 2, except that strontium carbonate having a surface area of 19.0 m²/g and an alkali metal content of 20 ppm or less (manufactured by SAKAI CHEMICAL INDUSTRY CO., LTD under the trade name of SW-K20) was used as an alkaline earth metal carbonate. The reaction was carried out in a similar manner as in Example 1. The results are shown in Table 5.

Example 13

A catalyst was prepared in a similar manner as in Reference Example 2, except that strontium carbonate having a surface area of 41.3 m²/g and an alkali metal content of 20 ppm or less (manufactured by SAKAI CHEMICAL INDUSTRY CO., LTD under the trade name of SW-K40) was used as an alkaline earth metal carbonate. The reaction was carried out in a similar manner as in Example 1. The results are shown in Table 5.

TABLE 5

|  | Example 11 | Example 12 | Example 13 |
|---|---|---|---|
| Propylene conversion (%) | 2.3 | 3.6 | 1.6 |
| propylene oxide selectivity (%) | 44 | 40 | 32 |

Example 14

A catalyst was prepared in a similar manner as in Reference Example 1, except that barium carbonate having a surface area of 28.9 m²/g and an alkali metal content of 30 ppm or less (manufactured by SAKAI CHEMICAL INDUSTRY CO., LTD under the trade name of BW-KH30) was used as an alkaline earth metal carbonate. The reaction was carried out in a similar manner as in Example 1. The results are shown in Table 6.

Example 15

A catalyst was prepared in a similar manner as in Reference Example 2, except that barium carbonate having a surface area of 28.9 m²/g and an alkali metal content of 30 ppm or less (manufactured by SAKAI CHEMICAL INDUSTRY CO., LTD under the trade name of BW-KH30) was used as an alkaline earth metal carbonate. The reaction was carried out in a similar manner as in Example 1. The results are shown in Table 5.

TABLE 6

|  | Example 14 | Example 15 |
|---|---|---|
| Propylene conversion (%) | 3.1 | 1.8 |
| propylene oxide selectivity (%) | 30 | 33 |

INDUSTRIAL APPLICABILITY

An olefin oxide, which is industrially important as an intermediate material of industrial chemicals, synthetic resins, rubbers and the like can be produced selectively and efficiently.

The invention claimed is:

1. A process for producing an olefin oxide, comprising contacting an olefin and oxygen, in the presence of water and a halogen compound, with a silver catalyst,
wherein the silver catalyst is a silver catalyst that is obtainable by contacting silver metal, a silver compound or a mixture of both with an alkaline earth metal carbonate and that has an alkali metal content of 900 ppm or less based on the total weight of the silver catalyst; and
wherein the amount of water is from 0.2 mole to 10 moles per mole of the olefin.

2. The process for producing an olefin oxide according to claim 1, wherein, the halogen compound is an organohalogen compound, and the amount of the organohalogen compound is from 1 ppm to 1,000 ppm per mole of the olefin.

3. The process for producing an olefin oxide according to claim 1, wherein the content of silver in the silver catalyst is 0.1% by weight or more.

4. The process for producing an olefin oxide according to claim 1, wherein the content of silver in the silver catalyst is 0.5% by weight or more.

5. The process for producing an olefin oxide according to claim 1, wherein the silver catalyst is a silver-containing composition obtainable by calcining a silver-containing composition obtainable by contacting silver metal, a silver compound or a mixture of both with an alkaline earth metal carbonate.

6. The process for producing an olefin oxide according to claim 5, wherein the calcination is carried out at 70° C. or higher to 250° C. or lower under gas flow containing 5% to 70% of steam.

7. The process for producing an olefin oxide according to claim 1, wherein the silver metal is silver metal obtainable by contacting a silver compound with a reducing agent.

8. The process for producing an olefin oxide according to claim 1, wherein the alkaline earth metal carbonate is an alkaline earth metal carbonate having a specific surface area of 10 m²/g to 70 m²/g as measured by nitrogen absorption using a BET method.

9. The process for producing an olefin oxide according to claim 1, wherein the olefin is propylene and the olefin oxide is propylene oxide.

10. A process for producing an olefin oxide,
comprising contacting an olefin and oxygen, in the presence of water and a halogen compound, with a silver catalyst, wherein the silver catalyst is a silver catalyst that is obtainable by contacting silver metal, a silver compound or a mixture of both with an alkaline earth metal carbonate and that has an alkali metal content of 1,500 ppm or less based on the total weight of the silver catalyst;

wherein the silver catalyst is a silver-containing composition obtainable by calcining a silver-containing composition obtainable by contacting silver metal, a silver compound or a mixture of both with an alkaline earth metal carbonate; and wherein the calcination is carried out at 70° C. or higher to 250° C. or lower under gas flow containing 5% to 70% of steam.

* * * * *